(12) United States Patent
Christophersen et al.

(10) Patent No.: US 6,417,393 B1
(45) Date of Patent: Jul. 9, 2002

(54) PHENYL DERIVATIVES CONTAINING AN ACIDIC GROUP, THEIR PREPARATION AND THEIR USE AS CHLORIDE CHANNEL BLOCKERS

(75) Inventors: Palle Christophersen, Ballerup; Ove Pedersen, Ringsted, both of (DK)

(73) Assignee: Neurosearch A/S, Glostrup (DK)

( * ) Notice: Subject to any disclaimer, the term of this patent is extended or adjusted under 35 U.S.C. 154(b) by 0 days.

(21) Appl. No.: 09/194,083

(22) PCT Filed: May 26, 1997

(86) PCT No.: PCT/EP97/02723

§ 371 (c)(1),
(2), (4) Date: Jan. 22, 1999

(87) PCT Pub. No.: WO97/45400

PCT Pub. Date: Dec. 4, 1997

(30) Foreign Application Priority Data

May 24, 1996 (DK) .............................. 0602/96
Apr. 22, 1997 (DK) .............................. 0452/97

(51) Int. Cl.$^7$ .......................................... C07C 241/00
(52) U.S. Cl. ..................... 562/439; 560/34; 514/535
(58) Field of Search ..................... 562/439; 560/34; 514/535

(56) References Cited

U.S. PATENT DOCUMENTS

| | | |
|---|---|---|
| 2,722,544 A | 11/1955 | Feuerthalen |
| 3,784,564 A | 1/1974 | Rohr et al. |
| 3,798,268 A | 3/1974 | Tweit |
| 4,405,644 A | 9/1983 | Kabbe et al. |
| 4,468,380 A | 8/1984 | O'Doherty et al. |
| 4,994,493 A | 2/1991 | Greger et al. |
| 5,489,612 A | 2/1996 | Atwood et al. |
| 6,204,294 B1 | 3/2001 | Bryan et al. |

FOREIGN PATENT DOCUMENTS

| | | |
|---|---|---|
| DE | 2315302 A | 10/1974 |
| DE | 2928485 A | 1/1981 |
| GB | 828231 A | 2/1960 |
| GB | 1055786 | 1/1967 |
| GB | 1055786 A | 1/1967 |
| GB | 1139343 A | 1/1969 |
| GB | 1139343 | 1/1969 |
| JP | 55162757 | 12/1980 |
| JP | 8216526 | 8/1996 |
| WO | 94 22807 | 10/1994 |
| WO | WO9422807 A | 10/1994 |
| WO | 9608242 A | 3/1996 |
| WO | WO9608242 A | 3/1996 |

OTHER PUBLICATIONS

Carling et al, Journal of Medicinal Chemistry, vol. 36, No. 22, 1993, pp. 3397–3408.
Staiger et al, Journal of Organic Chemistry, pp. 1427–1439, 1953.
Koenig, J. Prakt. Chem., vol. 2, No. 69, 1904, p. 33.
Leitch et al., Can. J. Res. Sect. B. vol. 23, 1945, p. 139, 155.
Fahmy et al., Egypt. J. Chem., vol. 20, 1977, pp. 259,265, 266, 275.

(List continued on next page.)

*Primary Examiner*—Paul J. Killos
(74) *Attorney, Agent, or Firm*—Birch, Stewart, Kolasch & Birch, LLP

(57) ABSTRACT

The present patent application relates to compounds having formula (I) or a pharmaceutically acceptable salt thereof wherein one of $R^1$, $R^2$ and $R^3$ is a non-cyclic acidic group having a pKa value below 8 or a group which is in vivo convertible to such a group; $R^4$, $R^5$ and the other two of the substituents $R^1$, $R^2$ and $R^3$ are each independently selected from hydrogen, alkyl, cycloalkyl, cycloalkylalkyl, alkenyl, alkynyl, alkoxy, hydroxy, halogen, trifluoromethyl, trifluoromethoxy, cyano, nitro, amnino, and aryl, aralkyl, arylamino, aryloxy, aryl—CO—, or heteroaryl, wherein the aryl and heteroaryl groups may be substituted one or more times with substituents selected from alkyl, cycloalkyl, cycloalkylalkyl, alkenyl, alkynyl, hydroxy, alkoxy, halogen, trifluoromethyl, trifluoromethoxy, cyano, nitro and amino; or $R^3$ and $R^4$ or $R^4$ and $R^5$ together form a fused 4- to 7-membered carbocyclic ring which may be unsaturated, or partially or fully saturated, while the other substituents $R^1$, $R^2$, $R^3$, $R^4$ and $R^5$ are as defined above; Y is —CO—, —CS—, —SO$_2$—, or —C(=N—R$^8$)—, wherein $R^8$ is hydrogen, alkyl, or cyano; X is —NH—, —CH$_2$—NH—, or —SO$_2$—NH—; Z is NR$^6$, O, —CH=CH—, —C=C—, —N=CH—, or —CH=N—; wherein $R^6$ is hydrogen, or alkyl; $R^{11}$, $R^{12}$, $R^{13}$, $R^{14}$ and $R^{15}$ are each independently selected from hydrogen, alkyl, cycloalkyl, cycloalkylalkyl, alkenyl, alkynyl, alkoxy, hydroxy, halogen, trifluoromethyl, trifluoromethoxy, cyano, nitro, amino, —NHSO$_2$—R$^7$, —COOR$^7$, —SO$_2$N(R$^7$)$_2$, —SO$_2$OR$^7$ and —CO—R$^7$, wherein $R^7$ is hydrogen alkyl, cycloalkyl, cycloalkylalkyl, alkenyl, alkynyl, aryl or aralkyl; and aryl, aralkyl, arylamino, aryloxy, aryl-CO—, or heteroaryl, wherein the aryl and heteroaryl groups may be substituted one or more times with substituents selected from alkyl, cycloalkyl, cycloalkylalkyl, alkenyl, alkynyl, hydroxy, alkoxy, halogen, trifluoromethyl, trifluoromethoxy, cyano, nitro and amino; or one of $R^{11}$ and $R^{12}$, $R^{12}$ and $R^{13}$, $R^{13}$ and $R^{14}$ or $R^{14}$ and $R^{15}$ together form a fused 4- to 7-membered carbocyclic ring which may be unsaturated, or partially or fully saturated, while the other substituents $R^{11}$, $R^{12}$, $R^{13}$, $R^{14}$ and $R^{15}$ are as defined above. The compounds are useful for the treatment of diseases and disorders responsive to the blockage of chloride channels.

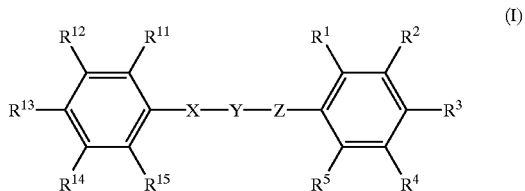

(I)

12 Claims, No Drawings

OTHER PUBLICATIONS

Wangemann et al., Chemical Abstracts, vol. 107, No. 11, Sep. 14, 1987.

Wangemann, P. et al., Chemical Abstracts, vol. 107, p. 21 (Sep. 14, 1987).

R. W. Carling et al., Journal of Medicinal Chemistry, vol. 36, 3397–3408 (1993).

R.P. Staiger et al., Journal of Organic Chemistry, pp. 1427–1439 (1953).

Leitch et al., Database Crossfire, (Abstract) XP 2038038, 1945.

Fahmy et al., Database Crossfire, (Abstract) XP 2038039, 1977.

Koenig, Database Crossfire, (Abstract) XP 2038037, 1964.

Minami, Toshiaki et al., Jpn. Kokai Tokkyo Koho, Abstract # 1996:533975 (1996).

Shaw, Kenneth, Braz. Pedido PI, Abstract # 1994:409421 (1994).

Widdowson, Katherine Louisa et al., PCT/US96/02260 (claims), (1996).

O'Doherty, George O. P., Can., Abstract # 1985:100800 (1985).

Gulubov, A. et al., U.S., Abstract # 88:16166 (1978).

Galabov, A. S. et al., Fr. Demande, Abstract # 1973:462220 (1973).

Gulubov, Angel S. et al., Ger. Offen. Abstract # 1973:400870 (1973).

Taylor, P.J., J. Chem. Soc., (B) 1968, pp. 1554–1559.

Fahmy, A.F.M., Indian J. Chem., vol. 11, No. 9 (1973) pp. 871–873. (Abstract).

PHENYL DERIVATIVES CONTAINING AN ACIDIC GROUP, THEIR PREPARATION AND THEIR USE AS CHLORIDE CHANNEL BLOCKERS

This application is the national phase under 35 U.S.C. §371 of prior PCT International Application No. PCT/EP97/02723 which has an International filing date of May 26, 1997 which designated the United States of America.

The present invention relates to phenyl derivatives which are valuable blockers of chloride channels and as such useful for the treatment of sickle cell anaemia, brain oedema following ischaemia or tumours, diahreea, hypertension (diuretic) and for the reduction of the intraocular pressure for the treatment of disorders such as glaucoma. The compounds of the invention may also be useful in the treatment of allergic or inflammatory conditions and for the promotion of wound healing.

BACKGROUND

Chloride channels serve a wide variety of specific cellular functions and contribute to the normal function of skeletal and smooth muscle cells. Blockers of chloride channels are known to be useful in the treatment of brain oedema following ischaemia or tumours, diahreea, hypertension (diuretic) and for the reduction of the intraocular pressure in disorders such as glaucoma.

Sickle cell anaemia and the existence of sickle haemoglobin was the first genetic disease to be understood at the molecular level. The genetic defect underlying sickle cell anaemia causes the substitution of a single amino acid resulting in a mutant haemoglobin, sickle haemoglobin.

The physical manifestations of sickle cell disease is anaemia and painful ischaemic crises due to occlusion of the microcirculation by deformed erythrocytes (sickle cells). The primary cause of sickle erythrocyte deformation and distortion (or sickling) is a reversible polymerisation and gelation of sickle haemoglobin induced at the low oxygen tensions prevalent in metabolically active tissues. Sickle cells are also characterised by an enhanced cation permeability, resulting in cation depletion and cellular dehydration. Since the delay time for the polymerisation has been described as an extremely steep function of the sickle haemoglobin concentration itself, any decrease in cell volume will greatly increase the probability of sickling and thereby of vessel occlusion. Compounds which blocks the deoxygenation induced salt and volume (water) loss may delay the sickling process enough to avoid occlusion upon the passage of the sickle erythrocyte through metabolically active tissue. It has been estimated that a delay time of only 10 sec may suffice.

Several membrane ion channels and transporters present in normal erythrocytes has been suggested to participate in the altered membrane permeabilities of sickle cells. The favoured hypothesis has been stimulation of the $Ca^{2+}$-activated $K^+$-channel and several blockers of this channel has been suggested as therapeutic agents for the treatment of sickle-cell anaemia (Effects of Cetiedil on Monovalent Cation Permeability in the Erythrocyte: An explanation for the Efficacy of Cetiedil in the treatment of Sickle Cell Anaemia, Berkowitz, L. R., Orringer, E. P., Blood cells, (283–288 (1982) and U.S. Pat. No. 5.273.992). Since, $K^+$ efflux through a K-channel must be followed by an equal efflux of $Cl^-$ to maintain electroneutrality, blockade of erythrocyte chloride channels are predicted to be as effective as blocking the K-channels itself. An advantage to the use of chloride channel blockers is that salt loss which may occur due to activation of unknown K-channel types will indirectly be blocked too.

The compounds of the present invention are valuable blockers of chloride channels as determined by concomitant measurements of conductive netfluxes of chloride and membrane potentials in suspensions of erythrocytes, and the compounds are therefore predicted to be useful for the treatment of ailments responsive to the blockade of chloride channels, including sickle cell anaemia.

The use of blockers of chloride channels for the treatment of sickle-cell anaemia form a new therapeutic approach.

Several chloride channel blockers and the use thereof have already been described in the technical literature:

Pflügers Arch (1986), 407 (suppl. 2), pages 128–141 describe several compounds with chloride channel blocking activity. A very potent compound described herein is 5-nitro-2-(3-phenylpropylamino)benzoic acid. The reference do not disclose the use of chloride channel blockers for the treatment of sickle cell anaemia.

U.S. Pat. No. 5,489,612 describes Calixarene derivatives and their use as chloride channel blockers.

U.S. Pat. No. 4.994.493 describes certain 5-nitrobenzoic acid derivatives and their use in the treatment of cerebral oedema.

WO 96/16647 describes the use of chloride channel blockers for the reduction of the intraocular pressure and specifically the use of chloride channel blockers for the treatment of glaucoma.

OBJECTS OF THE INVENTION

It is an object of the present invention to provide a series of phenyl derivatives carrying an acidic group and pharmaceutically acceptable salts thereof which are useful in the treatment of disorders or diseases responsive to the blockade of chloride channels.

Still another object of the present invention is to provide a method of treating disorders or diseases responsive to the blockade of chloride channels, such as for example brain oedema following ischaemia or tumours, diahreea, hypertension (diuretic), glaucoma and in particular sickle-cell anaemia. A further object of the present invention is to provide a method for the treatment of allergic or inflammatory conditions and for the promotion of wound healing.

SUMMARY OF THE INVENTION

The invention then comprises, inter alia, alone or in combination:

A compound having the formula

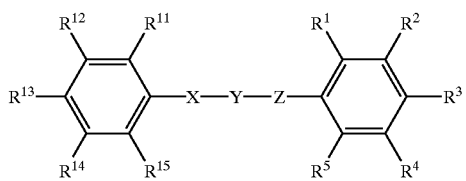

or a pharmaceutically acceptable salt thereof wherein
one of $R^1$, $R^2$ and $R^3$ is a non-cyclic acidic group having a pKa value below 8 or a group which is in vivo convertible to such a group; $R^4$, $R^5$ and the other two of the substituents $R^1$, $R^2$ and $R^3$ are each independently selected from hydrogen; alkyl; cycloalkyl;

cycloalkylalkyl; alkenyl; alkynyl; alkoxy; hydroxy; halogen; trifluoromethyl; trifluoromethoxy; cyano; nitro; amino; and aryl, aralkyl, arylamino, aryloxy, aryl-CO—, or heteroaryl, wherein the aryl and heteroaryl groups may be substituted one or more times with substituents selected from alkyl, cycloalkyl, cycloalkylalkyl, alkenyl, alkynyl, hydroxy, alkoxy, halogen, trifluoromethyl, trifluoromethoxy, cyano, nitro and amino; or $R^3$ and $R^4$ or $R^4$ and $R^5$ together form a fused 4 to 7 membered carbocyclic ring which may be unsaturated, or partially or fully saturated, while the other substituents $R^1$, $R^2$, $R^3$, $R^4$ and $R^5$ is as defined above;.

Y is —CO—, —CS—, —SO$_2$—, or —C(=N—R$^8$)—, wherein $R^8$ is hydrogen, alkyl, or cyano;

X is —NH—, —CH$_2$—NH—, or —SO$_2$—NH—;

Z is NR$^6$, O, —CH=CH—, —C≡C—, —N=CH—, or —CH=N—; wherein $R^6$ is hydrogen, or alkyl;

$R^{11}$ $R^{12}$, $R^{13}$, $R^{14}$ and $R^{15}$ are each independently selected from hydrogen; alkyl; cycloalkyl; cycloalkylalkyl; alkenyl; alkynyl; alkoxy; hydroxy; halogen; trifluoromethyl; trifluoromethoxy; cyano; nitro; amino; —NHSO$_2$—R$^7$, —COOR$^7$, —SO$_2$N(R$^7$)$_2$, —SO$_2$OR$^7$ and —CO—R$^7$, wherein $R^7$ is hydrogen, alkyl, cycloalkyl, cycloalkylalkyl, alkenyl, alkynyl, aryl or aralkyl; and aryl, aralkyl, arylamino, aryloxy, aryl-CO—, or heteroaryl, wherein the aryl and heteroaryl groups may be substituted one or more times with substituents selected from alkyl, cycloalkyl; cycloalkylalkyl; alkenyl; alkynyl; hydroxy, alkoxy, halogen, trifluoromethyl, trifluoromethoxy, cyano, nitro and amino; or one of $R^{11}$ and $R^{12}$, $R^{12}$ and $R^{13}$, $R^{13}$ and $R^{14}$ or $R^{14}$ and $R^{15}$ together form a fused 4 to 7 membered carbocyclic ring which may be unsaturated, or partially or fully saturated, while the other substituents $R^{11}$, $R^{12}$, $R^{13}$, $R^{14}$ and $R^{15}$ is as defined above;.

a compound as above wherein one of $R^1$, $R^2$ and $R^3$ is NH$_2$, —COOR$^9$, —CH$_2$COOR$^9$, —CONH$_2$, —NHSO$_2$—R$^9$, —SO$_2$N(R$^9$)$_2$, —SO$_2$OR$^9$, —PO$_3$H$_2$, —PO$_3$RH, —PO$_2$NH$_2$, —CONHOH, —CONHCN, —CONH$_2$SO$_2$R$^9$ and —CONHNH$_2$, wherein $R^9$ is hydrogen, alkyl, cycloalkyl, cycloalkylalkyl, alkenyl, alkynyl, aryl or aralkyl, and the other of $R^1$, $R^2$ and $R^3$ is as defined above;

a pharmaceutical composition comprising a therapeutically effective amount of a compound as above or a pharmaceutically acceptable salt thereof together with at least one pharmaceutically acceptable carrier or diluent;

the use of a compound as above for the preparation of a medicament for the treatment of a disorder or disease of a living animal body, including a human, which disorder or disease is responsive to the blockade of chloride channels;

the use of a compound as above for the preparation of a medicament for the treatment of sickle-cell anaemia, brain oedema following ischaemia, or tumours, diahreea, hypertension (diuretic), glaucoma, allergic or inflammatory conditions and ulcers;

a method for the treatment of a disorder or disease of a living animal body, including a human, which disorder or disease is responsive to the blockade of chloride channels, comprising administering to a living animal body in need thereof a therapeutically effective amount of a compound as above;

a method for the treatment of a disorder or disease of a living animal body which disorder or disease is sickle-cell anaemia, brain oedema following ischaemia, or tumours, diahreea, hypertension (diuretic), glaucoma, allergic or inflammatory conditions and ulcers comprising administering to such a living animal body, including a human, in need thereof a therapeutically effective amount of a compound as above;

a method for the preparation of a compound as above, comprising:

a) reacting a compound having the formula

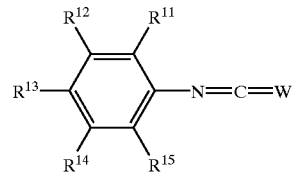

wherein W is O, or S and $R^{11}$, $R^{12}$, $R^{13}$, $R^{14}$ and $R^{15}$ is as defined above, with a compound having the formula

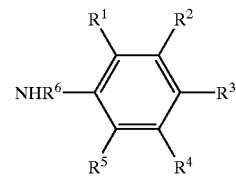

wherein $R^1$, $R^2$, $R^3$, $R^4$, $R^5$ and $R^6$ is as defined above, or b) reacting a compound having the formula

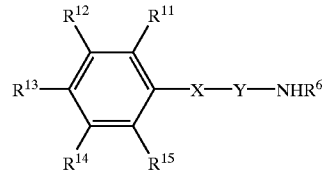

wherein X, Y, $R^6$, $R^{11}$, $R^{12}$, $R^{13}$, $R^{14}$ and $R^{15}$ is as defined above, with a compound having the formula

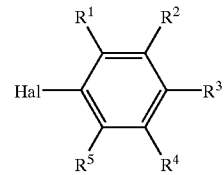

wherein Hal is halogen and $R^1$, $R^2$, $R^3$, $R^4$ and $R^5$ is as defined above, whereafter the compound obtained is optionally converted to another compound of the invention and/or a pharmaceutically acceptable salt thereof is formed using conventional methods; and the use of blockers of chloride channels of erythrocytes for the treatment of sickle cell anaemia.

Examples of pharmaceutically acceptable addition salts include inorganic and organic acid addition salts such as the hydrochloride, hydrobromide, phosphate, nitrate, perchlorate, sulfate, citrate, lactate, tartrate, maleate, fumarate, mandelate, benzoate, ascorbate, cinnamate, benzenesulfonate, methanesulfonate, stearate, succinate, glutamate, glycollate, toluene-p-sulphonate, formate, malonate, naphthalene-2-sulphonate, salicylate and the acetate. Such salts are formed by procedures well known in the art.

Other acids such as oxalic acid, while not in themselves pharmaceutically acceptable, may be useful in the preparation of salts useful as intermediates in obtaining compounds of the invention and their pharmaceutically acceptable acid addition salts.

Halogen is fluorine, chlorine, bromine or iodine.

Alkyl means a straight chain or branched chain of one to six carbon atoms, including but not limited to, methyl, ethyl, propyl, isopropyl, butyl, isobutyl, t-butyl, pentyl, and hexyl; methyl, ethyl, propyl and isopropyl are preferred groups.

Cycloalkyl means cyclic alkyl of three to seven carbon atoms, including but not limited to cyclopropyl, cyclobutyl, cyclopentyl, and cyclohexyl;

Cycloalkylalkyl means cycloalkyl as above and alkyl as above, meaning for example, cyclopropylmethyl.

Alkenyl means a group of from two to six carbon atoms, including at least one double bond, for example, but not limited to ethenyl, 1,2- or 2,3-propenyl, 1,2-, 2,3-, or 3,4-butenyl.

Alkynyl means a group of from two to six carbon atoms, including at least one triple bond, for example, but not limited to ethynyl, 1,2-, 2,3-propenyl, 1,2-,2,3- or 3,4-butenyl.

Alkoxy is O-alkyl, wherein alkyl is as defined above.

Amino is $NH_2$ or NH-alkyl or N-(alkyl)$_2$, wherein alkyl is as defined above.

A non-cyclic acidic group having a pKa below 8 or a group which is in vivo convertible to such group include groups such as $NH_2$, —$COOR^9$, —$CH_2COOR^9$, —$CONH_2$, —$NHSO_2$—$R^9$, —$SO_2N(R^9)_2$, —$SO_2OR^9$, —$PO_3H_2$, —$PO_3RH$, —$PO_2NH_2$, —CONHOH, —CONHCN, —$CONH_2SO_2R^9$ and —$CONHNH_2$, wherein $R^9$ is hydrogen, alkyl, cycloalkyl, cycloalkylalkyl, alkenyl, alkynyl, aryl or aralkyl.

Heteroaryl is a 5- or 6-membered heterocyclic monocyclic group. Such a monocyclic heteroaryl group includes, for example, oxazol-2-yl, oxazol-4-yl, oxazol-5-yl, isoxazol-3-yl, isoxazol-4-yl, isoxazol-5-yl, thiazol-2-yl, thiazol-4-yl, thiazol-5-yl, isothiazol-3-yl, isothiazol-4-yl, isothiazol-5-yl, 1,2,4-oxadiazol-3-yl, 1,2,4-oxadiazol-5-yl, 1,2,4-thiadiazol-3-yl, 1,2,4-thiadiazol-5-yl, 1,2,5-oxadiazol-3-yl, 1,2,5-oxadiazol-4-yl, 1,2,5-thiadiazol-3-yl, 1,2,5-thiadiazol-4-yl, 1-imidazolyl, 2-imidazolyl, 4-imidazolyl, 1-pyrrolyl, 2-pyrrolyl, 3-pyrrolyl, 2-furanyl, 3-furanyl, 2-thienyl, 3-thienyl, 2-pyridyl, 3-pyridyl, 4-pyridyl, 2-pyrimidinyl, 4-pyrimidinyl, 5-pyrimidinyl, 3-pyridazinyl, 4-pyridazinyl, 2-pyrazinyl, 1-pyrazolyl, 3-pyrazolyl, and 4-pyrazolyl.

Aryl means an aromatic group such as phenyl or naphtyl.

Aralkyl means arylalkyl wherein alkyl and aryl is as defined above, meaning for example benzyl, or phenethyl.

I.p. means intraperetoneally, which is a well known route of administration.

P.o. means peroral, which is a well known route of administration.

Further, the compounds of this invention may exist in unsolvated as well as in solvated forms with pharmaceutically acceptable solvents such as water, ethanol and the like. In general, the solvated forms are considered equivalent to the unsolvated forms for the purposes of this invention.

It will be appreciated by those skilled in the art that the compounds of the present invention contain several chiral centres and that such compounds exist in the form of isomers (i.e. enantiomers). The invention includes all such isomers and any mixtures thereof including racemic mixtures.

Some of the compounds of the present invention exist in (+) and (−) forms as well as in racemic forms. Racemic forms can be resolved into the optical antipodes by known methods, for example, by separation of diastereomeric salts thereof with an optically active acid, and liberating the optically active amine compound by treatment with a base. Another method for resolving racemates into the optical antipodes is based upon chromatography on an optically active matrix. Racemic compounds of the present invention can thus be resolved into their optical antipodes, e.g., by fractional crystallization of d- or l- (tartrates, mandelates, or camphorsulphonate) salts for example. The compounds of the present invention may also be resolved by the formation of diastereomeric amides by reaction of the compounds of the present invention with an optically active activated carboxylic acid such as that derived from (+) or (−) phenylalanine, (+) or (−) phenylglycine, (+) or (−) camphanic acid or by the formation of diastereomeric carbamates by reaction of the compounds of the present invention with an optically active chloroformate or the like.

Additional methods for the resolvation of optical isomers, known to those skilled in the art may be used, and will be apparent to the average worker skilled in the art. Such methods include those discussed by J. Jaques, A. Collet, and S. Wilen in "Enantiomers, Racemates, and Resolutions", John Wiley and Sons, New York (1981).

The compounds of the invention may be prepared in numerous ways. The compounds of the invention and their pharmaceutically acceptable derivatives may thus be prepared by any method known in the art for the preparation of compounds of analogous structure, and as shown in the representative examples which follow.

Biology

The compounds of the present invention are potent blockers of chloride channels in normal as well as sickle cell erythrocytes. The ability of the compounds to block the erythrocyte chloride channels could not be demonstrated by classical electrophysiological measurements such as patch clamping, since the channel unit conductance is below the detection limit of these techniques.

All dose-response experiments were therefore performed by concomitant measurements of conductive netfluxes of $Cl^-$ ($J_{Cl}$) and membrane potentials ($V_m$) in suspensions of erythrocytes (Bennekou, P. and Christophersen, P. (1986), Flux ratio of Valinomycin—Mediated $K^+$ Fluxes across the Human Red Cell Membrane in the presence of the Protronophore CCCP. J. Membrane Biol. 93, 221–227. ). The membrane $Cl^-$-conductances were calculated by the following equation (Hodgkin, A. L. and Huxley, A. F. (1952) The components of membrane conductance in the giant axon of loligo. J. Physiol. Lond. 116, 449–472):

$$G_{Cl} = \frac{F * J_{Cl}}{(V_m - E_{Cl})}$$

where F is the Faraday constant and $E_{Cl}$ is the Nernst potential for the Cl-ion. Administration of N-(3-Trifluoromethylphenyl)-N'-(2-carboxyphenyl) urea to a suspension of normal erythrocytes blocked $G_{Cl}$ more than 95% with an $IC_{50}$-value of 0.6 μM. The compound equipotently blocked $G_{Cl}$ from oxygenated as well as deoxygenated homozygoteous sickle cell erythrocytes.

Experimentally induced cell volume losses were measured as changes in the relative volume of packed cells. Inducing a massive water and salt loss (KCl) by addition the $K^+$-ionophore valinomycin to the suspension for 5 min reduced the cell volume by 26%. N-(3-Trifluoromethylphenyl)-N'-(2-carboxyphenyl) urea dose-dependently ($IC_{50}$-value of 1.2 $\mu$M) reduced the volume loss to 7%.

Deoxygenation induced permeability increases of sickle cells were estimated by measuring the extracellular $K^+$-concentration vs time. Normal erythrocytes exhibited very small $K^+$-fluxes, which was insensitive to deoxygenation and insensitive to 10 $\mu$M N-(3-Trifluoromethylphenyl)-N'-(2-carboxyphenyl) urea. The $K^+$ flux from oxygenated sickle erythrocytes was 2–3 times higher than from normal erythrocytes and these fluxes was accelerated 4–8 times upon deoxygenation. In presence of N-(3-Trifluoromethylphenyl)-N'-(2-carboxyphenyl) urea (10 $\mu$M) the basal $K^+$-flux from sickle erythrocytes was normalised and the deoxygenation induced flux component were nearly abolished.

N-(3-Trifluoromethylphenyl)-N'-(2-carboxyphenyl) urea was non-toxic to mice at concentrations up to 150 mg/kg i.p. and i.v.

Pharmaceutical Compositions

While it is possible that, for use in therapy, a compound of the invention may be administered as the raw chemical, it is preferable to present the active ingredient as a pharmaceutical formulation.

The invention thus further provides pharmaceutical formulations comprising a compound of the invention or a pharmaceutically acceptable salt or derivative thereof together with one or more pharmaceutically acceptable carriers therefor and, optionally, other therapeutic and/or prophylactic ingredients. The carrier(s) must be "acceptable" in the sense of being compatible with the other ingredients of the formulation and not deleterious to the recipient thereof.

Pharmaceutical formulations include those suitable for oral, rectal, nasal, topical (including buccal and sub-lingual), vaginal or parenteral (including intramuscular, subcutaneous and intravenous) administration or in a form suitable for administration by inhalation or insufflation.

The compounds of the invention, together with a conventional adjuvant, carrier, or diluent, may thus be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed. Formulations containing ten (10) milligrams of active ingredient or, more broadly, 0.1 to one hundred (100) milligrams, per tablet, are accordingly suitable representative unit dosage forms.

The compounds of the present invention can be administrated in a wide variety of oral and parenteral dosage forms. It will be obvious to those skilled in the art that the following dosage forms may comprise, as the active component, either a compound of the invention or a pharmaceutically acceptable salt of a compound of the invention.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding capacity in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as admixture of fatty acid glycerides or cocoa butter, is first melted and the active component is dispersed homogeneously therein, as by stirring. The molten homogenous mixture is then poured into convenient sized molds, allowed to cool, and thereby to solidify.

Formulations suitable for vaginal administration may be presented as pessaries, tampons, creams, gels, pastes, foams or sprays containing in addition to the active ingredient such carriers as are known in the art to be appropriate.

Liquid form preparations include solutions, suspensions, and emulsions, for example, water or water-propylene glycol solutions. For example, parenteral injection liquid preparations can be formulated as solutions in aqueous polyethylene glycol solution.

The compounds according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilising and/or dispersing agents. Alternatively, the active ingredient may be in powder form, obtained by aseptic isolation of sterile solid or by lyophilisation from solution, for constitution with a suitable vehicle, e.g. sterile, pyrogen-free water, before use.

Aqueous solutions suitable for oral use can be prepared by dissolving the active component in water and adding suitable colorants, flavours, stabilizing and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavours, stabilizers, buffers, artificial and natural sweeteners, dispersants, thickeners, solubilizing agents, and the like.

For topical administration to the epidermis the compounds according to the invention may be formulated as ointments, creams or lotions, or as a transdermal patch.

Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Formulations suitable for topical administration in the mouth include lozenges comprising active agent in a flavoured base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions are applied directly to the nasal cavity by conventional means, for example with a dropper, pipette or spray. The formulations may be provided in single or multidose form. In the latter case of a dropper or pipette, this may be achieved by the patient administering an appropriate, predetermined volume of the solution or suspension. In the case of a spray, this may be achieved for example by means of a metering atomising spray pump.

Administration to the respiratory tract may also be achieved by means of an aerosol formulation in which the active ingredient is provided in a pressurised pack with a suitable propellant such as a chlorofluorocarbon (CFC) for example dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

In formulations intended for administration to the respiratory tract, including intranasal formulations, the compound will generally have a small particle size for example of the order of 5 microns or less. Such a particle size may be obtained by means known in the art, for example by micronization. When desired, formulations adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Tablets or capsules for oral administration and liquids for intravenous administration are preferred compositions.

Methods of Treating

The compounds of the present invention are, due to their potent chloride channel blocking activity, useful in the treatment of sickle cell anaemia, brain oedema following ischaemia or tumors, diahreea, and hypertension (diuretic) as well as other disorders responsive to the blockade of chloride channels. The compounds of the invention may also be useful in the treatment of allergic and inflammatory conditions, for the promotion of wound healing or the treatment of ulcers. The compounds of this invention may accordingly be administered to a living animal body, including a human, in need of treatment, alleviation, or elimination of an indication associated with or responsive to chloride channel blocking activity. This includes especially sickle cell anaemia, brain oedema following ischaemia or tumors, diahreea, and hypertension (diuretic).

Suitable dosage range are 0.1–500 milligrams daily, and especially 10–70 milligrams daily, administered once or twice a day, dependent as usual upon the exact mode of administration, form in which administered, the indication toward which the administration is directed, the subject involved and the body weight of the subject involved, and further the preference and experience of the physician or veterinarian in charge.

The following examples will illustrate the invention further, however, they are not to be construed as limiting.

EXAMPLE 1

3'-Trifluoromethylphenyl-2-carboxyphenyl Urea

3'-Triflouromethylphenyl isocyanate (1.87 g, 10 mmol) and 2-aminobenzoic acid (1.37 g, 10 mmol) were in toluene (50 mL) until the 2-aminobenzoic acid had been consumed. After cooling to room temperature the product was filtered off. M.p. 171–172° C.

The following compounds were prepared analogously:

3'-Trifluoromethylphenyl-3-carboxyphenyl urea. M.p. 183–185° C.

2'-Methoxy-5'-chlorophenyl-3-carboxyphenyl urea.

3'-Trifluoromethylphenyl-2-carboxy-5-nitrophenyl urea. M.p. 206–207° C.

3'-Trifluoromethylphenyl-5-chloro-2-nitrophenyl urea. (intermediate)

3'-Trifluoromethylphenyl-2-carboxy-4-methylphenyl urea. M.p. 183–184° C.

3'-Trifluoromethylphenyl-4-bromo-2-carboxyphenyl urea. M.p. 199–200° C.

3'-Trifluoromethylphenyl-3-carbamoylphenyl urea. M.p. 205–206° C.

3'-Trifluoromethylphenyl-3-sulfamoylphenyl urea. M.p. 184–185° C.

3'-Trifluoromethylphenyl-5-chloro-2-phenylsulfonamidocarbonylphenyl urea. M.p. 270–300° C. (dec.)

3'-Trifluoromethylphenyl-2-methylsulfonamidocarbonylphenyl urea.

3'-Trifluoromethylphenyl-6-methyl-2-carboxyphenyl urea. M.p. 166° C.

3'-Trifluoromethylphenyl-3-methyl-2-carboxyphenyl urea. M.p. 181–182° C.

3'-Trifluoromethylphenyl-4-hydroxy-2-carboxyphenyl urea. M.p. 166–167° C.

4'-Nitrophenyl-2-carboxyphenyl urea. M.p. 203–204° C.

3'-Trifluoromethylphenyl-2-carboxymethylphenyl urea. M.p. 182–183° C.

3'-Trifluoromethylphenyl-2-sulfophenyl urea. M.p. 182—183° C.

3'-Trifluoromethylphenyl-2-carboxyphenyl thiourea. M.p. 210–220° C.

3'-Trifluoromethylphenyl-2-carboxy-5-trifluoromethylphenyl urea. M.p. 179° C.

3'-Trifluoromethylphenyl-4,5-dimethoxy-2-carboxyphenyl urea. M.p. 198–199° C.

3'-carboxyphenyl-2-hydroxy-5-chlorophenyl urea. M.p. 216° C.

3'-carbamoylphenyl-2-hydroxy-5-chlorophenyl urea. M.p. 203–204° C.

3'-Trifluoromethylphenyl-2-hydroxy-4-nitro-5-carboxyphenyl urea. M.p. 201—203° C.

EXAMPLE 2

(intermediate)

2-Chloro-5-hydroxybenzoic Acid

5-Amino-2-chlorobenzoic acid (85%, 10 g, 49.7 mmol) was suspended in diluted sulphuric acid (1.25%, 800 mL) and cooled to 5° C. on an ice bath. Sodium nitrite (59,72 mmol) dissolved in water (150 mL) was added slowly while keeping the temperature of the reaction below 5° C. After addition of the sodium nitrite the reaction was stirred for another 45 min at 5–10° C. until a clear solution was obtained. The reaction mixture was poured into hot (70–85° C.) water (1.5 L), charcoal added and the reaction mixture heated at reflux for 25 min. Filtration and extraction with ethyl acetate afforded 6.7 g of the desired product as light brown crystals

EXAMPLE 3

(intermediate)

2-Chloro-3-hydroxy-4-nitro-benzoic Acid

To a solution of 2-chloro-5-hydroxybenzoic acid (6.5 g, 38 mmol) in cold acetic acid (150 mL) was added concentrated nitric acid (2.7 mL, 38 mmol). After addition the reaction mixture was stirred for 30 min at room temperature then heated at 35° C. for 20 min. The reaction mixture was poured into ice and the product filtered off to give 1.5 g of the desired compound as yellow crystals.

EXAMPLE 4

(intermediate)

4-Amino-6-chloro-3-hydroxybenzoic Acid

2-Chloro-3-hydroxy-4-nitro-benzoic acid (2.2 g, 10 mmol) dissolved in ethanol (120 mL) was reduced over Raney-Ni to give 1.7 g of black crystals.

EXAMPLE 5

3'-Trifluoromethylphenyl-4-carboxy-5-chloro-2-hydroxyphenyl Urea

4-Amino-6-chloro-3-hydroxybenzoic acid (1.6 g, 8.6 mmol) and 3-tifluoromethylphenyl isocyanate (1.2 mL, 9 mmol) were mixed in toluene (100 mL). The reaction was heated at reflux for 2 hr. The cooled reaction was filtered. The crude product was dissolved in ethanol at reflux and treated with activated charcoal. Subsequent re-crystallisation from ethyl acetate afforded the 1.2 g of the desired compound. M.p. 267–268° C.

EXAMPLE 6

3'-Trifluoromethylphenyl-2-amino-5-chlorophenyl Urea

3-Trifluoromethylphenyl-5-chloro-2-nitrophenyl urea (4.0 g, 11 mmol) was dissolved in ethanol (200 mL). Raney-Ni (approx. 2 g) was added and the reaction hydrogenated for 4 hr at room temperature. Filtration and evaporation of the solvent afforded 3.2 g of the desired compound as light pink crystals.

EXAMPLE 7

3'-Trifluoromethylphenyl-5-chloro-2-methanesulfonylaminophenyl Urea

3'-Trifluoromethylphenyl-2-amino-5-chlorophenyl urea (0.5 g, 1.5 mmol), methanesulphonylchloride (1.19 mL, 2.5 mmol), pyridine (0.4 mL, 5 mmol) and tetrahydrofuran (25 m) were mixed and heated at reflux for 5 hr. The reaction mixture was poured into water and extracted with ethyl acetate. The crude product was purified by column chromatography on silica gel using toluene/ethyl acetate (1:1) as eluent. 0.1 g of the desired material was obtained. M.p. 185–186° C.

EXAMPLE 8

3'-Trifluoromethylphenyl-2-carboxyphenyl Urea Isopropyl Ester

To 3'-trifluoromethylphenyl-2-carboxyphenyl urea (3.24 g, 10 mmol) was added thionyl chloride (15 mL). After heating the reaction at 50° C. for 1 hr the excess thionyl chloride was evaporated. The residue was stirred up in diethyl ether and filtered off to give 2.9 g of the desired acid chloride. The acid chloride (1.5 g) was added to isopropanol (15 mL). The reaction was stirred at room temperature overnight. The solvent was evaporated and the residue re-crystallised from ethanol (96%, 20 mL) to give 0.65 g of the desired material. M.p. 137–138° C.

Analogously were made:

3'-Trifluoromethylphenyl-2-carboxyphenyl urea methyl ester. M.p. 169–170° C.

3'-Trifluoromethylphenyl-2-hydrazinocarbonylphenyl urea. M.p. 172–173° C.

3'-Trifluoromethylphenyl-2-hydroxylaminocarbonylphenyl urea. M.p. 210–212° C.

EXAMPLE 9

2-(3'-Trifluoromethylbenzylcarboxamido)benzoic Acid

To 3-trifluoromethylphenyl acid (2.70 g, 13.2 mmol) in diethyl ether (100 mL) was added thionyl chloride (2 mL, 27 mmol). After heating at reflux for 1 hr the reaction mixture was evaporated to dryness. The residue was dissolved in diethyl ether and 2-aminobenzoic acid (1.85 g, 13.5 mmol) was added followed by triethylamine (5 mL). After stirring for 30 min water was added and the organic phase washed

EXAMPLE 10

(intermediate)

2-methylsulfonamidocarbonylaniline

Lithium methanesulfonamidate (1.0 g, 10 mmol) and isatoic anhydride (1.63 g, (10 mmol) in dimethyl sulfoxide (5 mL) were heated at 80° C. for 30 min. The reaction was cooled down to room temperature and acidified with hydrogen chloride in diethyl ether. The ether was evaporated and water added. The precipitated oil was purified by column chromatography on silica gel eluting with ethyl acetate/methanol (95:5). The desired material was obtained in a yield of 0.52 g.

Analogously were made;

2-phenylsulfonamidocarbonylaniline

EXAMPLE 11

3'-Trifluoromethylphenyl-4-carboxyphenyl Urea

3'-Triflouromethylphenyl isocyanate (1.7 mL, 10 mmol) and 4-aminobenzoic acid (1.37 g, 10 mmol) were stirred in dimethyl sulfoxide (20 mL) for 30 min. The reaction mixture was poured into water. The precipitate was filtered off and washed with water. The filter cake was stirred up in 4 N sodium hydroxide and filtered through celite. The filtrate was acidified and the precipitate filtered off. Washing with water and drying in the air afforded 3.0 g of the desired material. M.p. >300° C.

Analogously were made:

3'-Trifluoromethylphenyl-2-carboxy-4-nitrophenyl urea. M.p. 185–186° C.

3'-Trifluoromethylphenyl-2-carboxynapht-3-yl urea. M.p. 197–198° C.

3'-Trifluoromethylphenyl-4-methoxy-2-carboxyphenyl urea. M.p. 175–176° C.

3'-Methoxyphenyl-2-carboxyphenyl urea. M.p. 162–163° C. (dec.).

4'-Bromophenyl-2-carboxyphenyl urea. M.p. 153–154° C. (dec.).

3'-Nitrophenyl-2-carboxyphenyl urea. M.p. 190–191° C. (dec.).

2'-Methoxyphenyl-2-carboxyphenyl urea. M.p. 160–161° C. (dec.).

4'-Methoxyphenyl-2-carboxyphenyl urea. M.p. 175–17° C. (dec.).

1'-Naphthyl-2-carboxyphenyl urea.

2'-Trifluoromethylhenyl-2-carboxyphenyl urea. M.p. 172–163° C. (dec.).

4'-Methylphenylsulfonyl-2-carboxyphenyl urea. M.p. 166–168° C. (dec.).

EXAMPLE 12

(intermediate)

Ethyl N-(2-bromoethyl)aminobenzoate

Dibromomethane (21.5 mL, 0.25 mol), ethyl-2-aminobenzoate (3.7 mL, 0.25 mmol) and triethylamine (4.2 mL, 30 mmol) were mixed in dimethylformamide (50 mL) and heated at 110° C. for five hours. After cooling to room temperature the reaction was poured onto ice and extracted with diethyl ether. The organic solution was washed with water, dried over magnesium sulphate and evaporated to dryness. The residue was purified by column chromatography on silica gel using dichloromethane as eluent to give 3.3 g of the desired material.

EXAMPLE 13

N'-(3-Trifluoromethylphenyl)-N-(2-ethyloxycarbonylphenyl)-1,2-diaminoethane

Ethyl N-(2-bromoethyl)aminobenzoate (3.3 g, 12 mmol), 3-aminobenzotriflouride (1.5 mL, 12 mmol) and triethylamine (2 mL, 14 mmol) were mixed in dimethylformamide (25 mL). The reaction mixture was heated at 110° C. for five hours. The cooled reaction mixture was poured into water and extracted with diethyl ether. Purification by column chromatography on silica gel using dichloromethane as eluent gave 1.6 g of the desired material.

EXAMPLE 14

N-(3-Trifl uoromethyl)phenyl-N'-(2-carboxy) phenylsulfamide

A mixture of 3-acetamidobenzotrifluoride (3.0 g, 15 mmol) and 60% sodium hydride (0.6 g, 15 mmol) was stirred in toluene overnight at 60° C. A solution of thionyl chloride (1.2 mL, 15 mmol) in petroleum ether (10 mL) was added to the mixture while keeping the temperature below 8° C. After stirring at 6–8° C. for 2 hr the reaction was filtered and the filtrate evaporated to dryness. The residue was dissolved in diethyl ether (50 mL) and 2-aminobenzoic acid (2.0 g, 15 mmol) was added. After heating the reaction at reflux for 13 hr the solvent was evaporated. The residue was heated to reflux in 2 N sodium hydroxide. The reaction was acidified and the precipitate filtered off. Purification by column chromatography on silica gel using ethyl acetate as eluent gave the desired compound. M.p. 162–163° C.

EXAMPLE 15

3'-Trifluoromethylbenzyl-2-carboxyphenyl Urea

To a solution of di-tert-butyl dicarbonate (0.68 g, 3.13 mmol) in methylene chloride (25 mL) were added dimethylaminopyridine (36 mg, 0.3 mmol) and 3-trifluoromethylbenzylamine (0.43 mL, 3 mmol). After stirring for 20 min at room temperature 2-aminobenzoic acid (0.43 g, 3.13 mmol) was added. The reaction was heated at reflux overnight. The solvent was evaporated and the residue dissolved in ethyl acetate. The solution was washed with 1 M hydrochloric acid and water. The solvent was evaporated and the residue suspended in water. 4 N Sodium hydroxide (1.25 mL, 5 mmol) was added. The resulting suspension was washed with diethyl ether and acidified with 4 N hydrochloric acid. The precipitate was filtered off and washed with water. Re crystallisation from aqueous ethanol gave 80 mg of the desired material. M.p. 176–178° C.

The compound 3'-trifluoromethyl-4-phenylphenyl-2-carboxyphenyl urea, M.p. 191–192° C. (dec.), was prepared analogously.

EXAMPLE 16

(intermediate)

2-Amino-4-phenylbenzonitrile

A mixture of 2-amino-5-bromobenzonitrile (1.0 g, 5 mmol), phenylboronic acid (0.92 g, 7.5 mmol), tetrakis (triphenylphosphine)palladium (50 mg) and potassium carbonate (3.5 g, 25 mmol) in dimethoxyethane/water 2:1 (60 mL) was heated at reflux for 4 hours. After cooling to room temperature the reaction was diluted with water and extracted with ethyl acetate. The organic phase was dried and solvent evaporated. Trituration with petroleum ether gave 0.89 g of the desired compound.

EXAMPLE 17

2-(3'-Trilluoromethylphenyloxycarbonylamino) benzoic Acid

To a solution of 1.9 M phosgene in toluene (6.3 mL, 12 mmol) was added 3-hydroxybenzotrifluoride (1.62 g, 10 mmol) in toluene (30 mL) followed by triethyl amine (1.7 mL, 12 mmol) in toluene. After stirring for 15 min 2-aminobenzoic acid (1.37 g, 10 mmol) was added. >The reaction was stirred overnight at room temperature. The precipitate was filtered off and washed successively with water, toluene and petroleum ether to give 1.0 g of the title compound. M.p. 150–152° C.

EXAMPLE 18

3'-Trifluoromethylphenyl-5-chloro-2-aminophenyl Urea

To a solution of 3'-trifluoromethylphenyl-5-chloro-2-nitrophenyl urea (1.0 g, 2.8 mmol) in ethanol (50 mL) was added Raney-nickel. After stirring overnight the reaction was filtered and the filtrate evaporated to dryness to give 0.8 g pink crystals. M.p. 308° C.

What is claimed is:
1. A compound having the formula

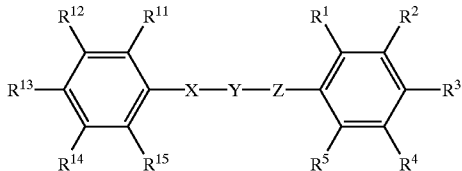

or a pharmaceutically acceptable salt thereof wherein
one of $R^1$ or $R^2$ is a non-cyclic acidic group having a pKa value below 8 or a group which is in vivo convertible to such a group;

$R^3$ and $R^4$ and the other of the substituents $R^1$ or $R^2$ are each independently selected from hydrogen; alkyl; cycloalkyl; cycloalkylalkyl; alkenyl; alkynyl; alkoxy; hydroxy; halogen; trifluoromethyl; trifluoromethoxy; cyano; nitro; amino; and aryl, aralkyl, arylamino, aryloxy, aryl-CO—, or heteroaryl, wherein the aryl and heteroaryl groups may be substituted one or more times with substituents selected from alkyl, cycloalkyl, cycloalkylalkyl, alkenyl, alkynyl, hydroxy, alkoxy, halogen, trifluoromethyl, trifluoromethoxy, cyano, nitro and amino with the proviso that $R^3$ is not hydrogen;

or $R^3$ and $R^4$ or $R^4$ and $R^5$ together form a fused 4 to 7 membered carbocyclic ring which may be unsaturated, or partially or fully saturated, while the other substituents $R^1$, $R^2$, $R^3$, $R^4$ and $R^5$ are as defined above, with the proviso that $R^1$ is not OH or $R^1$ and $R^2$ are not $SO_2NH_2$;

$R^5$ is hydrogen;
Y is —CO—, —CS—, —$SO_2$—, or —C(=N—$R^8$)—, wherein $R^8$ is hydrogen, alkyl, or cyano;

X is —NH—, —$CH_2$—NH—, or —$SO_2$—NH—;
Z is $NR^6$, O, —CH=CH—, —C≡C—, —N=CH—, or —CH=N—; wherein $R^6$ is hydrogen, or alkyl;

$R^{12}$, $R^{13}$, and $R^{14}$ are each independently selected from hydrogen; alkyl; cycloalkyl; cycloalkylalkyl; alkenyl; alkynyl; alkoxy; hydroxy; halogen; trifluoromethyl; trifluoromethoxy; cyano; nitro; amino; —NHSO_2—$R^7$, —COOR$^7$, —SO_2N(R$^7$)$_2$, —SO_2OR$^7$ and —CO—R$^7$, wherein $R^7$ is hydrogen, alkyl, cycloalkyl, cycloalkylalkyl, alkenyl, alkynyl, aryl or aralkyl; and aryl, aralkyl, arylamino, aryloxy, aryl-CO—, or heteroaryl, wherein the aryl and heteroaryl groups may be substituted one or more times with substituents selected from alkyl, cycloalkyl; cycloalkylalkyl; alkenyl; alkynyl; hydroxy, alkoxy, halogen, trifluoromethyl, trifluoromethoxy, cyano, nitro and amino, with the proviso that $R^{12}$ is not hydrogen;

or one of $R^{12}$ and $R^{13}$ or $R^{13}$ and $R^{14}$ together form a fused 4 to 7 membered carbocyclic ring which may be unsaturated, or partially or fully saturated, while the other substituents $R^{12}$, $R^{13}$, and $R^{14}$ are as defined above;

$R^{11}$ and $R^{15}$ are both hydrogen;
with the further proviso that when X=NH, Y=CO and Z=NH, then $R^{12}$ and $R^2$ are not $SO_3H$ and $R^{13}$ and $R^3$ are not $NH_2$.

2. A compound according to claim 1 wherein one of $R^1$, $R^2$ and $R^3$ is $NH_2$, —COOR$^9$, —$CH_2COOR^9$, —CONH$_2$, —NHSO$_2$—$R^9$, —SO$_2$N(R$^9$)$_2$, —SO$_2$OR$^9$, PO$_3$H2, —PO$_3$RH, —PO$_2$NH$_2$, —CONHOH, CONHCN, —CONHSO$_2$R$^9$ and —COHNNH$_2$, wherein $R^9$ is hydrogen, alkyl, cycloalkyl, cycloalkylalkyl, alkenyl, alkynyl, aryl or aralkyl, and the other of $R^1$, $R^2$ and $R^3$ is as defined in claim 1 with the proviso that $R^1$, $R^2$ and $R^3$ is not $SO_2NH_2$.

3. A compound according to claim 1, said compound being
3'-Trifluoromethylphenyl-2-carboxy-4-methylphenyl urea;
3'-Trifluoromethylphenyl-4-bromo-2-carboxyphenyl urea;
3'-Trifluoromethylphenyl-4-hydroxy-2-carboxyphenyl urea;
3'-Trifluoromethylphenyl-4,5-dimethoxy-2-carboxyphenyl urea;
3'-Trifluoromethylphenyl-2-carboxy-4-nitrophenyl urea;
3'-Trifluoromethylphenyl-2-carboxynaphth-3-yl urea; or
3'-Trifluoromethylphenyl-4-methoxy-2-carboxyphenyl urea.

4. A pharmaceutical composition comprising a therapeutically effective amount of a compound of claim 1 or a pharmaceutically acceptable salt thereof together with at least one pharmaceutically acceptable carrier or diluent.

5. A method for the treatment of a disorder or disease of a living animal body, including a human, which disorder or disease is responsive to the blockade of chloride channels, comprising:
administering to said living animal body, including a human, an effective amount of the compound according to claim 3.

6. A method for the treatment of sickle-cell anaemia, brain oedema following ischaemia, or tumours, diahreea, hypertension (diuretic), glaucoma, allergic or inflammatory conditions and ulcers, comprising:
administering to a living animal body, including a human, an effective amount of the compound according to claim 1.

7. A method for the treatment of a disorder or disease of a living animal body, including a human, which disorder or disease is responsive to the blockade of chloride channels, comprising:

administering to a living animal body, including a human, in need thereof a therapeutically effective amount of a compound according to claim 1.

8. A method for the treatment of a disorder or disease of a living animal body which disorder or disease is sickle-cell anaemia, brain oedema following ischaemia, or tumours, diahreea, hypertension (diuretic), glaucoma, allergic or inflammatory conditions and ulcers comprising administering to such a living animal body, including a human, in need thereof a therapeutically effective amount of a compound according to claim 1.

9. A method for the treatment of sickle-cell anaemia comprising:

administering to a living animal body, including a human, an effective amount of a blocker of chloride channels of erythrocytes.

10. The method of claim 9, wherein said blocker of chloride channels of erythrocytes is 3'-Trifluoromethylphenyl-2-carboxy-4-methylphenyl urea;

3'-Trifluoromethylphenyl-4-bromo-2-carboxyphenyl urea;

3'-Trifluoromethylphenyl-4-hydroxy-2-carboxyphenyl urea;

3'-Trifluoromethylphenyl-4,5-dimethoxy-2-carboxyphenyl urea;

3'-Trifluoromethylphenyl-2-carboxy-4-nitrophenyl urea;

3'-Trifluoromethylphenyl-2-carboxynaphth-3-yl urea; or

3'-Trifluoromethylphenyl-4-methoxy-2-carboxyphenyl urea.

11. The method of claim 6, wherein said compound is administered to a human.

12. The method of claim 9, wherein said blocker is administered to a human.

\* \* \* \* \*